(12) United States Patent
McKay

(10) Patent No.: US 8,408,250 B2
(45) Date of Patent: Apr. 2, 2013

(54) BONE REPLACEMENT MATERIAL MIXING AND DELIVERY DEVICES AND METHODS OF USE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 519 days.

(21) Appl. No.: 12/818,300

(22) Filed: Jun. 18, 2010

(65) Prior Publication Data

US 2011/0308665 A1    Dec. 22, 2011

(51) Int. Cl.
B65B 1/04       (2006.01)
(52) U.S. Cl. .................. 141/27; 141/2; 141/23
(58) Field of Classification Search ............... 141/2, 18, 141/21, 23, 27; 606/93
See application file for complete search history.

(56) References Cited

U.S. PATENT DOCUMENTS

| | | | |
|---|---|---|---|
| 4,331,188 A * | 5/1982 | Reynaud | 141/311 R |
| 4,671,263 A | 6/1987 | Draenert | |
| 4,966,601 A | 10/1990 | Draenert | |
| 5,574,075 A | 11/1996 | Draenert | |
| 6,086,594 A | 7/2000 | Brown | |
| 6,361,539 B1 | 3/2002 | Heller et al. | |
| 6,395,006 B1 | 5/2002 | Burchett | |
| 6,696,073 B2 | 2/2004 | Boyce et al. | |
| 7,112,205 B2 * | 9/2006 | Carrison | 606/92 |
| 7,135,027 B2 | 11/2006 | Delmotte | |
| 7,160,020 B2 | 1/2007 | Sand | |
| 2002/0156483 A1 | 10/2002 | Voellmicke et al. | |
| 2003/0012079 A1 | 1/2003 | Coffeen et al. | |
| 2004/0267272 A1 * | 12/2004 | Henniges et al. | 606/93 |
| 2005/0113843 A1 | 5/2005 | Arramon | |
| 2007/0016215 A1 | 1/2007 | Wilander et al. | |
| 2008/0065088 A1 | 3/2008 | Hughes et al. | |
| 2008/0125722 A1 | 5/2008 | Hess et al. | |
| 2008/0172058 A1 | 7/2008 | Trieu et al. | |
| 2008/0188858 A1 | 8/2008 | Luzzi et al. | |
| 2009/0131908 A1 | 5/2009 | McKay | |
| 2009/0171362 A1 | 7/2009 | Schaeffer | |
| 2009/0281549 A1 | 11/2009 | Dixon | |
| 2009/0292290 A1 | 11/2009 | Truckai et al. | |
| 2010/0100099 A1 | 4/2010 | Reilly et al. | |

* cited by examiner

Primary Examiner — Gregory Huson
Assistant Examiner — Jason K Niesz

(57) ABSTRACT

Bone cement mixing and delivery devices and methods of using the devices are provided. The bone cement mixing and delivery devices and methods comprise a container having a bottom opening that can be sealed by a spacer in a syringe where movement of the plunger of the syringe moves the spacer away from the bottom opening in the container to dispense bone cement into the syringe. In some embodiments, the devices and methods increases efficiency and reduce the mess associated with transferring the bone cement to the syringe for delivery to a patient.

20 Claims, 6 Drawing Sheets

BONE REPLACEMENT MATERIAL MIXING AND DELIVERY DEVICES AND METHODS OF USE

BACKGROUND

Bone replacement material, such as bone cements, can be used during certain medical treatments to help repair and/or reconstruct bone (e.g., fractured bone). The ability of certain bone replacement material to repair and/or reconstruct bone can be enhanced by the inclusion of bioactive agents (e.g., bone morphogenic protein), which promote the growth of bone.

To prepare bone replacement material, a powdery substance is generally combined with a liquid, and the resultant combination is mixed together to form a bone cement paste. The bone cement paste can then be delivered to a treatment site (e.g., a fracture site) to help repair and/or reconstruct the bone.

Bone replacement material is typically added to a mortar and then undergoes a mixing process with a mixing element such as a blade, pestle or spatula. Once the desired consistency is reached, the bone replacement material is typically transferred from the mortar to a syringe by removing the plunger from the syringe and then transferring the bone replacement material using a spatula and placing it into the syringe barrel and then placing the plunger back in the syringe barrel. This process is time consuming, messy and often there is wastage of expensive bone replacement material not only left behind in the mortar but bone replacement material may also drip out on the outside of the syringe. There also may be an increased risk of environmental contamination (e.g., bacteria, viruses, particulates, etc.) by removing the plunger, as now the top inside of the barrel and the head of the plunger are exposed to the outside environment. Further, the user may set the plunger down to fill the syringe barrel, leaving it outside the sterile field, which may also cause contamination.

Often, with bone replacement material, such as bone cements, time consuming steps that delay the transfer of the bone cement from the mortar to the syringe may cause the bone cement to prematurely harden and thus render the bone cement useless for in vivo use.

Therefore, there is a need for bone replacement material mixing and delivery devices and methods that facilitate the mixing and transferring of substances that, when mixed, yield medically useful compositions. More specifically, there is a need for such devices that can conveniently and efficiently mix the component parts of bone replacement materials and transfer it to the syringe while reducing waste and contamination of the bone replacement materials.

SUMMARY

Methods and bone replacement material mixing devices are provided that increase the efficiency of transfer and delivery of bone replacement material because it takes less time for the user to transfer the bone replacement material into a syringe and less mess is involved in the transfer.

In some embodiments, the bone replacement material mixing devices help to reduce the amount of bone replacement material remaining in the container at the end of the mixing process. This can help to reduce the loss of expensive drug contents during the mixing and delivery process.

In some embodiments, the bone replacement material mixing devices allow for relatively easy transfer of the bone replacement material from the mixing container to the syringe for delivery to the patient. After mixing the bone replacement material, substantially all of the bone replacement material can be dispensed into the syringe.

In some embodiments, the bone replacement material mixing devices reduce the risk of contamination as the head or first end of the plunger can now be kept inside the syringe barrel thus avoiding further contamination of the syringe and plunger because the plunger is not being removed and the top of the barrel where the material is kept is not being exposed to environmental contamination (e.g., bacteria, viruses, particulates, etc.).

In one embodiment, there is a bone replacement material mixing and delivery device, comprising: a container for mixing and holding bone replacement material, the container having a top opening for addition of bone replacement material, a bottom surface, and at least one bottom opening disposed in the bottom surface of the container for transfer of bone replacement material out of the bottom surface of the container; a syringe configured to receive bone replacement material from the container for delivery to a patient, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position; and at least one spacer disposed within the syringe between the tip of the syringe and the first end of the plunger, the spacer movable with the plunger and configured to contact the at least one bottom opening of the container and seal it when the plunger is moved in the retracted position so as to prevent transfer of bone replacement material into the syringe, and the spacer configured to allow transfer of bone replacement material into the syringe when the first end of the plunger is moved to the extended position to open the at least one bottom opening of the container.

In another embodiment, there is a bone cement mixing device, comprising: a container for mixing and holding bone cement, the container having a top opening for addition and mixing of bone cement, a bottom surface, and at least one bottom opening disposed in the bottom surface of the container for transfer of bone cement out of the bottom surface of the container; a syringe configured to receive bone cement from the container, the syringe having a tip configured to be removably coupled to the at least one bottom opening of the container, the syringe comprising a plunger slidable within the syringe, the plunger having a first end and a second end, the second end configured for moving the first end of the plunger to at least a retracted position within the tip of the syringe and an extended position; and at least one spacer disposed within the syringe between the tip of the syringe and the first end of the plunger, the spacer contacting the first end of the plunger and movable with the plunger, the spacer being a shape complimentary to the tip of the syringe and a portion of the syringe under the tip and configured to contact the at least one bottom opening of the container and seal it when the plunger is moved in the retracted position so as to prevent transfer of bone cement into the syringe, and the spacer configured to allow transfer of bone cement into the syringe when the first end of the plunger moving to the extended position to move the spacer away from the at least one bottom opening of the container.

In yet another embodiment, there is a method for mixing and dispensing bone cement, the method comprising: providing a container to mix and dispense bone cement, the container having a top opening for addition of bone cement, a bottom surface, and at least one bottom opening disposed in the bottom surface of the container for dispensing bone cement out of the bottom surface of the container when it is mixed; providing a syringe configured to receive bone cement dispensed from the container, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position, the syringe containing at least one spacer disposed within the syringe between the tip and the first end of the plunger, the spacer movable with the plunger and configured to contact the at least one bottom opening of the container and seal it when the plunger is moved in the retracted position so as to prevent dispensing of bone cement into the syringe, and the spacer configured to allow dispensing of bone cement into the syringe when the first end of the plunger is moved to the extended position to open the at least one bottom opening of the container; coupling the syringe tip to the at least one bottom opening of the container; adding bone cement to the top opening of the container and mixing it in the container; and moving the plunger to the extended position to move the spacer away from the at least one bottom opening of the container to dispense the bone cement into the syringe.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
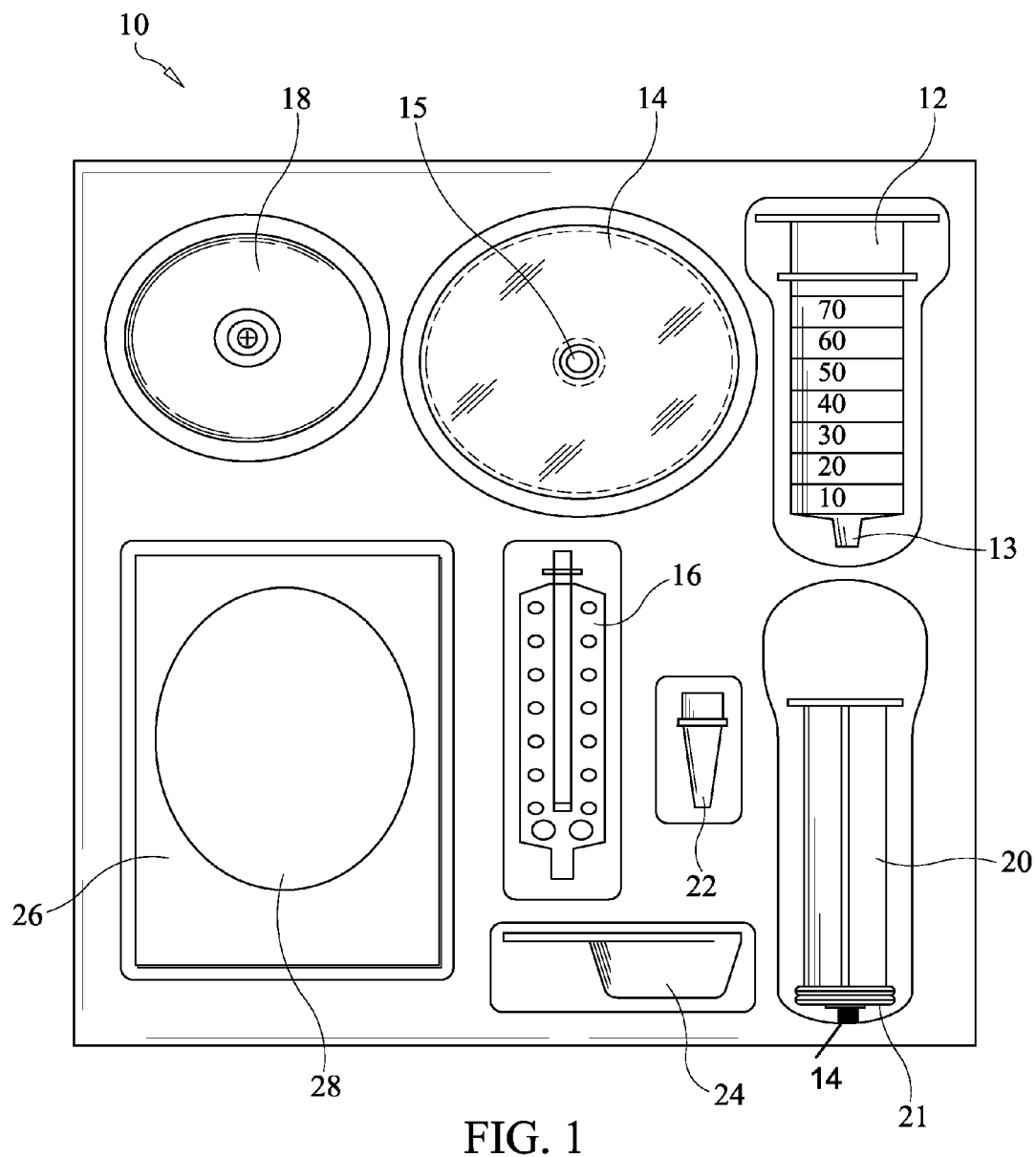
FIG. 1 is a plane view of an embodiment of a kit that contains the component parts of the bone replacement material mixing device.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a spacer" includes one, two, three or more spacers.

The term "practitioner" or "user" means a person who is using the methods and/or devices of the current disclosure on the patient. This term includes, without limitation, doctors (e.g., surgeons, interventional specialists, physicians), nurses, nurse practitioners, other medical personnel, clinicians, veterinarians, or scientists.

The term "mammal" refers to organisms from the taxonomy class "mammalian," including but not limited to humans, other primates such as chimpanzees, apes, orangutans and monkeys, rats, mice, cats, dogs, pigs, cows, horses, etc. In various embodiments, the mammal is a human patient.

The term "implantable" as utilized herein refers to a device (e.g., bone cement, bone replacement material, etc.) retaining potential for successful placement within a mammal.

Treating or treatment of a disease or condition refers to executing a protocol, which may include the use of the devices and methods herein and/or administering one or more bone materials to a patient (human, normal or otherwise, or other mammal), in an effort to diagnose and alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient.

In some embodiments, the bone cement mixing and delivery devices and methods provided comprise a container having a bottom opening that can be sealed by a spacer in a syringe where movement of the plunger of the syringe moves the spacer away from the bottom opening in the container to dispense bone cement into the syringe.

In some embodiments, the efficiency of transfer and delivery of the bone replacement material into the syringe device is increased because it takes less time for the user to transfer or dispense the bone replacement material into the syringe and less mess is involved in the transfer.

In some embodiments, the bone replacement material mixing device helps to reduce the amount of bone replacement material remaining in the container at the end of the mixing process. This can help to reduce the loss of expensive drug contents during the mixing and delivery process.

In some embodiments, the bone replacement material mixing device allows for relatively easy transfer of the bone replacement material from the mixing container to the syringe for delivery to the patient. After mixing the bone replacement material, substantially all of the bone replacement material can be dispensed into the syringe.

In some embodiments, the bone replacement material mixing device reduces the risk of contamination as the syringe plunger can now be kept inside the syringe barrel and this avoids further contamination of the syringe and plunger because it is not being removed and the top of the barrel that is in contact with the mixed material is not being exposed to outside air.

Mixing and Delivery Devices

In some embodiments, the bone replacement material mixing device is constructed for single use and/or is disposable. The bone replacement material mixing device can be relatively inexpensive and easy to use.

In one embodiment, there is a bone replacement material mixing and delivery device, comprising: a container for mixing and holding bone replacement material, the container having a top opening for addition of bone replacement material, a bottom surface, and at least one bottom opening disposed in the bottom surface of the container for transfer of bone replacement material out of the bottom surface of the container; a syringe configured to receive bone replacement material from the container for delivery to a patient, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position; and at least one spacer disposed within the syringe between the tip of the syringe and the first end of the plunger, the spacer movable with the plunger and configured to contact the at least one bottom opening of the container and seal it when the plunger is moved in the retracted position so as to prevent transfer of bone replacement material into the syringe, and the spacer configured to allow transfer of bone replacement material into the syringe when the first end of the plunger is moved to the extended position to open the at least one bottom opening of the container.

Referring to FIG. 1, it shows an embodiment of component parts of the mixing and delivery device, arranged as a kit 10, that are usable in association with each other to form a bone replacement material mixing and delivery device. In FIG. 1, the kit 10 includes a container 14 having at least one bottom opening 15 on its bottom surface. The container 14 is for receiving materials for mixing and for, after mixing, transferring or dispensing the materials in syringe 12 having syringe tip 13 that connects to the at least one bottom opening 15 of the container 14.

Figure 5:
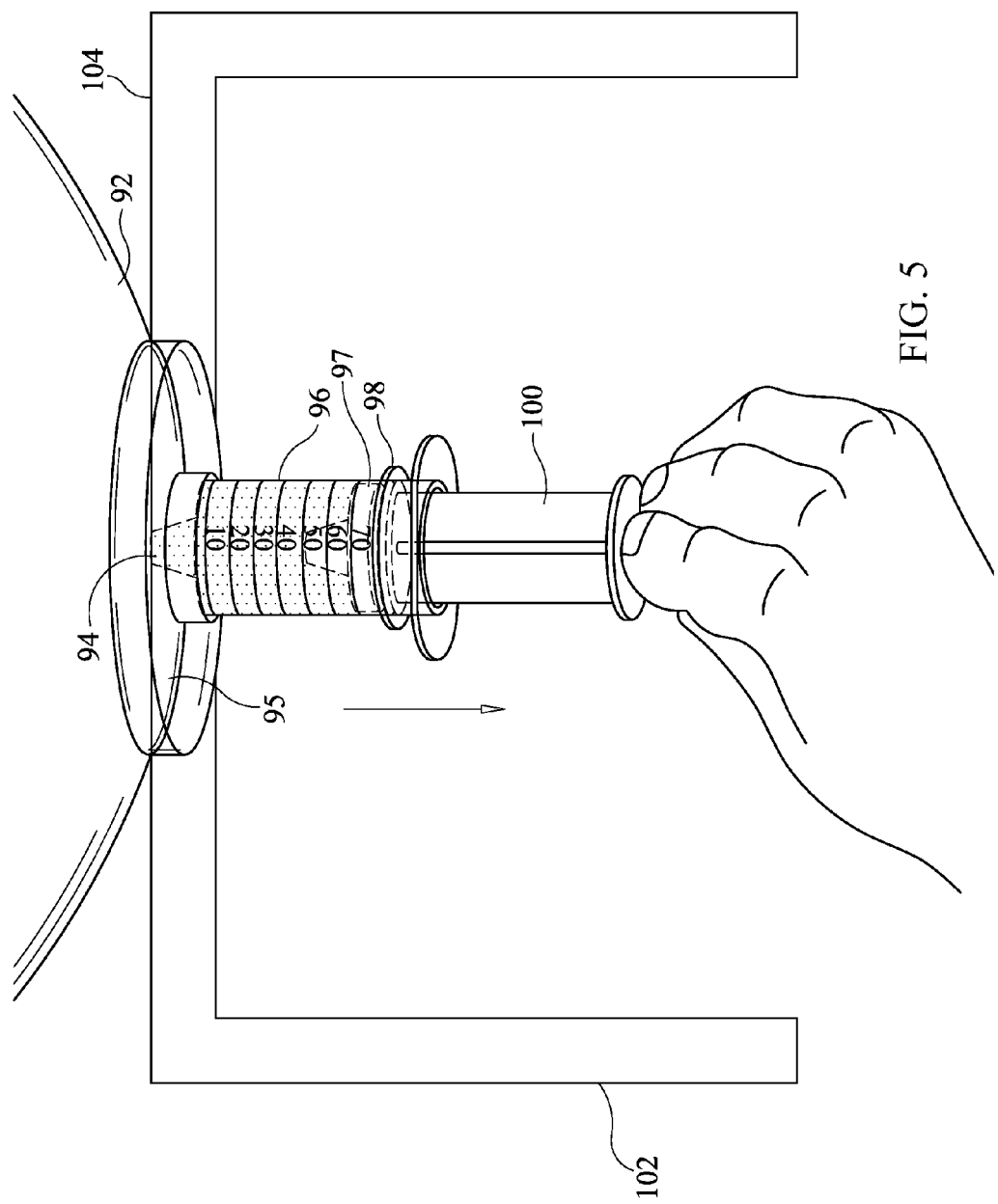
FIG. 5 is a perspective view of an embodiment of the container for mixing and holding the bone replacement material and the syringe attached to the bottom opening of the container. Here the cement has already been mixed and is ready for dispensing into the syringe. One hand is moving the plunger in an extended direction downward causing the spacer to move away from the bottom opening of the container and the pressure draws the bone replacement material into the syringe container for delivery to a patient.

Plunger 20 is configured to slide within syringe 12. The plunger has first end or head 21 and spacer 14 that is complementary to syringe tip 13 and fits snuggly within it. The spacer 14 acts to plug the at least one bottom opening 15 of the container 14 when the syringe tip 13 is removably attached to the at least one bottom opening 15 of the container. Often the syringe tip is in fluid communication with the opening 15 by a Luer Lock fitting or other connector. When the plunger 20 is in the retracted position the spacer 14 seals or plugs the bottom opening 15 in the container 14, and prevents bone replacement material from prematurely leaving the container before the components are mixed. The kit comes with a spatula 16 for mixing the bone replacement material while the plunger is in the retracted position and the spacer seals the bottom opening 15. In this way, the spacer provides a seal and prevents bone replacement material from leaving the container. The kit optionally can contain a measuring device 24 to measure materials placed in the container 14 for mixing, and a cover 18 that can be placed on top of the container 14. In some embodiments, the container can receive spatula 16 and by turning the cover 18, the user can mix the materials in the container. The kit optionally can also contain a dispensing element 22 (e.g., cannula, needle, tube) to dispense the mixed materials drawn into the syringe 13 from the container 15 and stand 26 that can be ergonomically designed for ease of use. The stand 26 can have an opening 28 to set the container 14 within it so that at least the container 14 and syringe 13 and plunger 20 stand upright for ease of use as shown in FIG. 5.

The components of the device (e.g., container, syringe, plunger, spacer, cannula, needle, legs, spatula, pestle, mixing blade, mixing piece, cover, and/or measuring device) may be made from materials, such as for example, polyurethane, polyurea, polyether(amide), PEBA, thermoplastic elastomeric olefin, copolyester, and styrenic thermoplastic elastomer, polypropylene, nylon, rubber, steel, aluminum, stainless steel, titanium, metal alloys with high non-ferrous metal content and a low relative proportion of iron, carbon fiber, glass fiber, plastics, ceramics or combinations thereof. The components can be the same or different colors or can be transparent or combinations thereof. The components may optionally include one or more tapered regions. The components will desirably be unaffected by contact with the bone replacement material and/or sterilizable by gamma radiation. Of course, various other alternative materials can be used, including materials which are capable of withstanding contact with monomer without significant degradation for limited periods of time.

Figure 2:
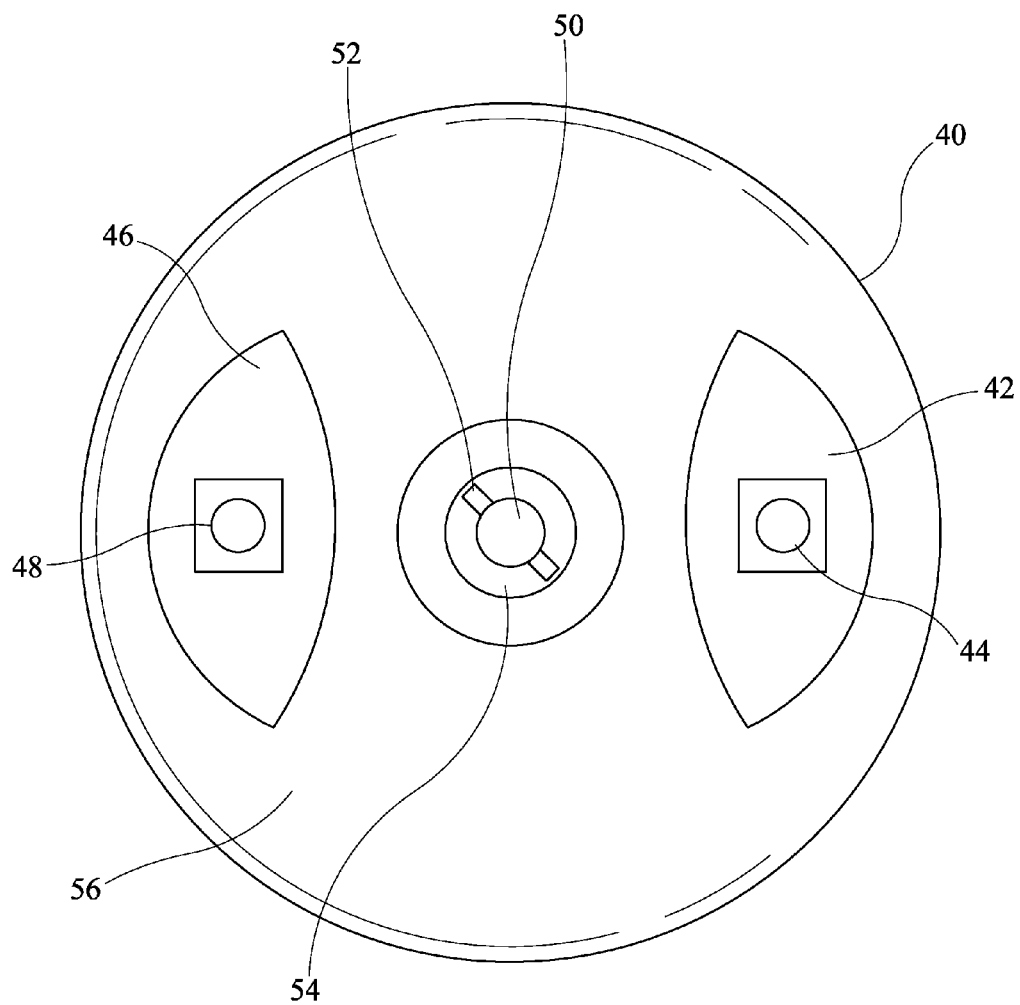
FIG. 2 is a bottom view of an embodiment of the container for mixing and holding the bone replacement material.

FIG. 2 is a bottom view of an embodiment of the exterior of the container 40 for mixing and holding the bone replacement material. The container has a top opening (not shown) that is configured to receive a mixing device (e.g., one or more mixing blades, spatulas, pestles, etc.). The mixing can be done by machine or by hand. The exterior of the container has side surface 46. Bottom surface 56 of the exterior of the container has an opening 50 that is surrounded by Leur Lock fitting 54 and the user attaches the tip of the syringe to the fitting at area 52, whereby turning the syringe and/or container causes the syringe to be in fluid communication with the container. The bottom surface of the container may have areas 42 and 46, which are areas to attach legs at 48 and 44, so that the container can stand in an upright position when the legs are attached.

Figure 3:
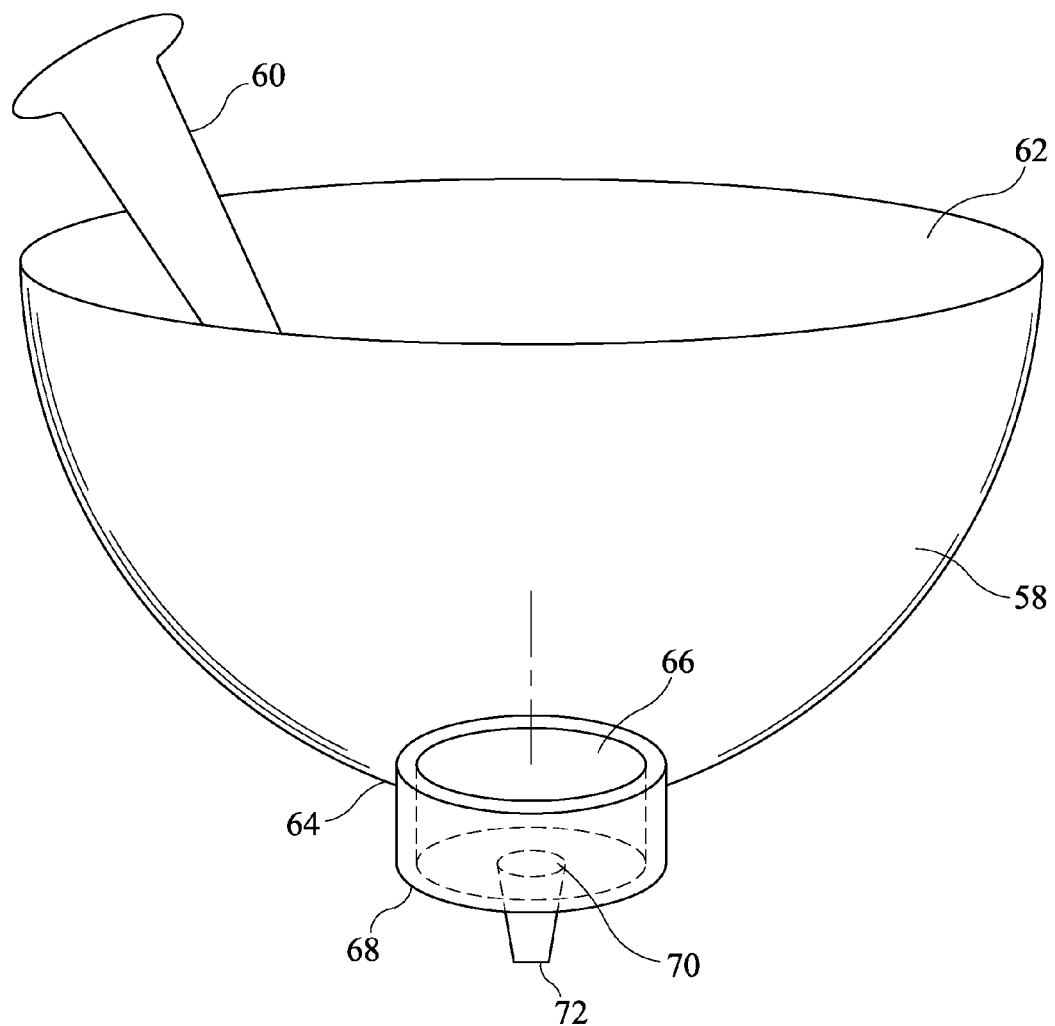
FIG. 3 is a side view of an embodiment of the container and a cross sectional view of the bottom opening of the container. A pestle used for mixing is shown in the container.

FIG. 3 is a side view of an embodiment of the container 58 having top opening 62 configured to receive a mixing element (e.g., automatic or manual mixer, blade, spatula, stirrer, pestle, etc.) and bone replacement material. In the embodiment shown, the container is a mortar or mixing bowl and the mixing element is a pestle 60. The bottom surface of the bowl 64 comprises at least one bottom opening 66 for transfer of the bone replacement material out the bottom opening. Around the bottom opening is a Leur Lock fitting 68 that is a diameter that allows a syringe to be removably coupled to the bottom opening. The Leur fitting can have a covering element 72 or cap that is removed and the syringe (not shown) and or mixing bowl is rotated clockwise or counterclockwise to align the bottom opening with the syringe and the spacer (not shown) in the syringe is configured to seal the bottom opening 66 to prevent bone replacement material from entering opening 70 and going into the syringe.

In some embodiments, the spacer is configured to either cover or plug the bottom opening of the container, when the diameter of the bottom opening is smaller than the diameter of at least a portion of the spacer that contacts the bottom opening. In this way a seal is produced when a portion of the spacer contacts the bottom opening of the container and thereby prevents bone replacement material from flowing out of the container and into the syringe. It will be understood that a portion of the spacer, or a surface of the spacer or all of the spacer may contact the bottom opening of the container to produce a fluid tight seal.

In some embodiments, the diameter of the bottom opening will be the same or larger diameter than a portion of the spacer, or a surface of the spacer or all of the spacer. In this way a portion of the spacer, or a surface of the spacer or all of the spacer may contact or penetrate the bottom opening of the container until it fits snuggly within it or mates with it to seal the bottom end opening until a liquid tight seal is achieved. The seal will prevent liquid from flowing out of the bottom opening of the container.

In some embodiments, the bottom opening, the plunger, and/or a portion of the spacer, or a surface of the spacer or all of the spacer may have a lubricant disposed on it for smooth movement.

After the bone replacement material is mixed the user pulls the plunger in a downward or substantially downward direction moving the spacer away from bottom end opening allowing gravity and the suction from the movement of the plunger to withdraw the mixed bone replacement material from the container through the bottom opening and into the syringe. To stop dispensing of the bone replacement material the user holds the plunger in a stationary position and prevents further material from entering the syringe. In this way, the bone replacement material can be easily and efficiently transferred to the syringe, avoiding the mess and without removing the plunger from the syringe. In some embodiments to produce or remove the seal of the bottom opening of the container, all the user has to do is move the plunger upward to break the seal and then downward to allow the material to transfer into the syringe.

In some embodiments, the syringe tip and the bottom opening can be configured to receive a removable cap. For example, after the bone replacement material is transferred into the syringe and the syringe is detached, the syringe tip can be capped before a cannula or needle is attached to the syringe tip or before delivery to a patient. The cannula or needle may also have a cap to prevent needle sticks. Likewise, in some embodiments, the container may have a removable cap disposed on the at least one bottom opening so that after the bone replacement material is transferred to the syringe and the syringe is detached, the bottom opening can be capped.

Figure 4:
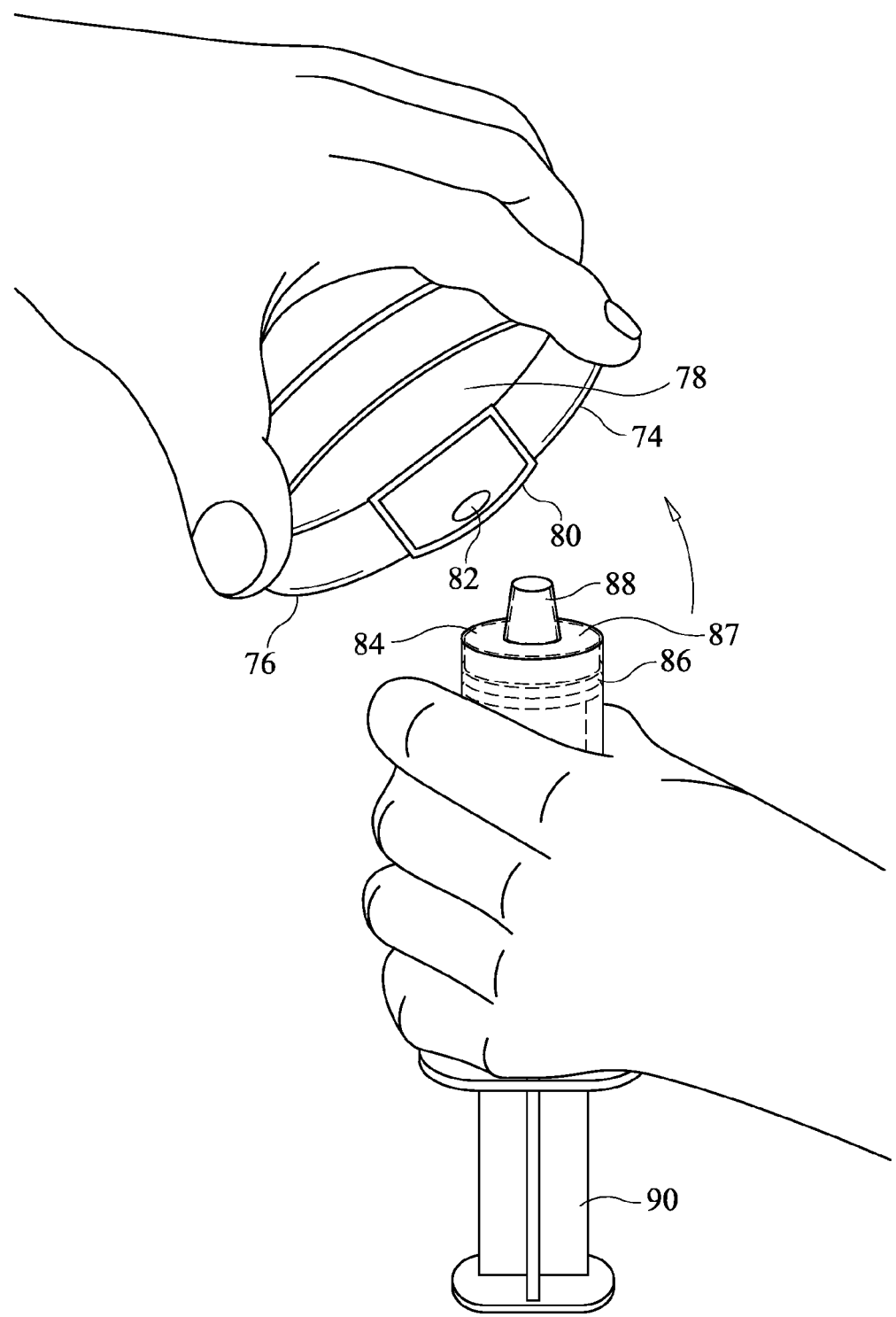
FIG. 4 is a perspective view of the assembly of an embodiment of the container for mixing and holding the bone replacement material and the syringe being removably attached to the bottom opening of the container. Here the container is being grasped by one hand and being manually rotated, and the syringe is being grasped by the other hand of the user, the rotation of the container and/or the syringe serves to removably attach the syringe to the container.

FIG. 4 is a perspective view of the assembly of an embodiment of the container 76 for mixing and holding the bone replacement material and the syringe 84 being removably attached to the bottom opening 82 of the container on the bottom surface 74 of the container. The container has interior 78 for mixing and holding bone replacement material in it. The container may include a Leur Lock fitting 80, for ease of removably attaching the syringe and fluidly coupling it to the bottom opening 82 of the container. The syringe has tip 88 at its top. The top has an opening in it configured to align with the bottom opening 82 of the container via Leur fitting 80. The syringe has a plunger where the first end 86 of the plunger can contact spacer 87. The spacer is disposed within the syringe barrel between the upper end of the plunger 86 and the syringe tip 88. The spacer 87 can be integral with the first end 86 of the plunger as one piece or alternatively, the first end 86 of the plunger can be coupled to it via an attachment means, such as an adhesive, mating pair, reciprocating threading, threading, screw, pin or other means. Alternatively the spacer 87 is a separate piece and as the user pushes the second end of the plunger 90 in an upward direction toward the container or in the retracted position, or pulls the second end of the plunger 90 in a downward direction away from the container or in an extended position, the spacer will move in the same direction as the plunger. In some embodiments, the spacer can be the rubber tip at the first end currently available on the plastic plungers of commercially available syringes. The rubber tip having the desired shape to fill the at least one bottom opening of the container.

The movement of the spacer 87 can be from direct contact with the first end of the plunger 86 or from air pressure within the syringe barrel that forces the spacer 87 in the direction that the plunger is moving. In the embodiment shown, the spacer 87 has a complementary shape to the tip 88 of the syringe and to the upper part of syringe 87. When the plunger is moved in a retracted position as shown in FIG. 4, the spacer 87 will provide a seal of the bottom opening 82 of the container and thus prevent or inhibit transfer of bone replacement material into the syringe 84.

In some embodiments, the spacer 87 may not only functions to seal or mate with the bottom opening 82, but may also enhance dispensing or expulsion of the bone replacement material from the syringe. In this way, the bone replacement material can be completely or incompletely expelled from the syringe and delivered to the patient as desired by the user. The spacer allows for efficient and easy delivery of the bone replacement material from the syringe.

The spacer can be made of rigid or soft material. In some embodiments, the spacer is deformable and will conform to the shape of the syringe and/or syringe tip as the plunger is pushed in an upward direction to seal the at least one bottom opening. The spacer may comprise polyurethane, polyurea, polyether(amide), PEBA, thermoplastic elastomeric olefin, copolyester, and styrenic thermoplastic elastomer, polypropylene, nylon, rubber (for example, the same rubber tip on plastic plungers that are currently available in syringes), steel, aluminum, stainless steel, titanium, metal alloys with high non-ferrous metal content and a low relative proportion of iron, carbon fiber, glass fiber, plastics, ceramics or combinations thereof. The spacer can be the same or different colors or can be transparent or combinations thereof.

In the embodiment shown in FIG. 4, the container 76 is being grasped by one hand and being manually rotated, and the syringe 84 is being grasped by the other hand of the user, the rotation of the container and/or the syringe serves to easily attach the syringe to the container by turning the syringe and/or container clockwise or counterclockwise depending on the embodiment. The bottom opening of the container and the opening of the syringe tip will then be aligned and once the spacer 87 is moved away from the bottom opening 82 transfer of the mixed bone replacement material can begin by gravity feed and suction from movement of the second end of the plunger 90 in a downward direction.

FIG. 5 is a perspective view of an embodiment of the assembled bone replacement material mixing and delivery device. The device is placed in a stand 104 and has legs 102 to hold the device in an upright position. The device comprises a container 92 for holding the bone replacement material. The bottom surface 95 has bottom opening 94 in an open or unsealed or unplugged position as spacer 97 (shown in broken lines) is being moved along with the first end of the plunger 98 from the retracted position to the extended position by the user moving the second end 100 of the plunger in a downward direction (shown by the arrow) away from the container. The bottom opening 94 once sealed by the spacer is now open and allows mixed bone replacement material 96 to fill or be dispensed into the syringe. The container may include a Leur Lock fitting or a snap fitting, or a push in fitting (not shown), for ease of removably attaching the syringe and fluidly coupling it to the bottom opening 94 of the container. The spacer 97 can be integral with the first end 98 of the plunger as one piece or alternatively, the first end 98 of the plunger can be coupled to it via an attachment means, such as an adhesive, mating pair, reciprocating threading, threading, snap fitting, or other means.

Alternatively the spacer 97 is a separate piece and as the user pushes the second end of the plunger 100 in an upward direction toward the container or in the retracted position, or pulls the second end of the plunger 100 in a downward direction away from the container or in an extended position, the spacer will move in the same direction as the plunger. It will be understood that the spacer can contact the entire surface of the first end of the plunger or it can contact a portion of the surface of the first end of the plunger.

The movement of the spacer 97 can be from direct contact with the first end of the plunger 98 or from air pressure within the syringe barrel that forces the spacer 97 in the direction that the plunger is moving. In the embodiment shown, the spacer 97 has a complementary shape to the upper part of syringe. When the plunger is moved in an extended position as shown in FIG. 5, the spacer 97 will not provide a seal and the bottom opening 94 of the container will allow transfer of bone replacement material into the syringe.

In some embodiments, the spacer 97 may not only functions to seal the bottom opening 94, but may also seal it and be flush with the bottom of the container so that the bone replacement material can be mixed in the container without worry that it will clog recesses or projections in the bottom of the container where material can invade. In some embodiments, the spacer 97 also enhances dispensing or expulsion of the bone replacement material from the syringe. In this way, the bone replacement material can be completely or incompletely expelled from the syringe and delivered to the patient as desired by the user. The spacer allows for efficient and easy delivery of the bone replacement material from the syringe.

In some embodiments, the spacer is flush with or exits the top of syringe when the plunger is in its retracted position. In some embodiments, the spacer is smaller in size and there is a space in the edge of the syringe tip. The spacer 97 fills the dead space in the syringe and provides easier delivery of the mixed bone replacement material.

The spacer can be any shape in a determined or regular form or configuration in contrast to an indeterminate or vague form or configuration (as in the case of a lump or other solid mass of no special form). Some shapes of the spacer include, square, rectangular, triangular, circular, spherical, substantially spherical, rod shaped, oval, or the like, they can be regular, geometric shapes to irregular, angled, or non-geometric shapes, or combinations of features having any of these characteristics. The spacer can be optimized to maximize the seal of the bottom opening, extend from the syringe (if desired), and/or expel materials from the syringe tip. In some embodiments, the spacer is a shape complementary to at least the tip of the syringe and/or upper part of the syringe. By "shape complementary" is meant that the spacer fits together with precision to at least the tip of the syringe and/or bottom opening of the container like a hand in a glove or a key into a lock, like mating pairs, like male female connectors or the like. The shape does not have to be 100% fit, but can be substantially complementary can be, 99%, 95%, 90%, or 85%, or 80% fit. For example, in some embodiments, the spacer fits within the syringe barrel and is substantially complementary in shape to the tip of the syringe, bottom opening of the container, and/or section just below the tip as shown by the broken lines 87 in FIG. 4 and 97 in FIG. 5. In some embodiments, the spacer can move vertically or up and down in the syringe, but can not tilt to the side or move horizontally in the syringe, when the syringe is coupled to the container.

In some embodiments, the spacer can extend from the tip of the syringe to seal the bottom opening of the container. In other embodiments, the spacer stays within the syringe. In some embodiments, the spacer has a portion that has a diameter that is the same or 1-5% smaller than the diameter of the syringe barrel, while a portion of the spacer is the same or 1-5% smaller than the diameter of the syringe tip to seal the bottom opening of the container. In some embodiments, the spacer is the same size or larger than the bottom opening of the container to provide an effective seal or plug.

FIG. 5 shows the bone replacement material 96 already mixed and is being dispensed into the syringe. One hand is moving the second end 100 of the plunger in an extended direction downward causing the spacer 97 to move away from the bottom opening 94 of the container and the pressure draws the bone replacement material 96 into the syringe container for delivery to a patient.

Figure 6:
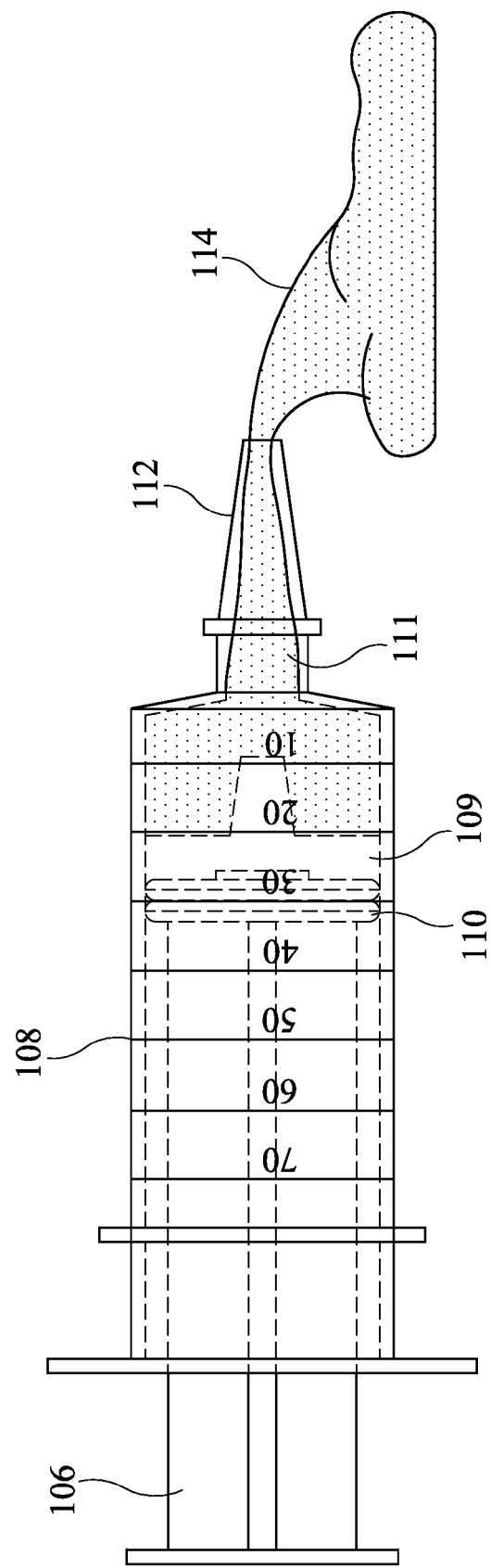
FIG. 6 is a perspective view of an embodiment of the mixed bone replacement material within the syringe being delivered.

After the mixed bone replacement material is drawn into the syringe, it can be delivered to the patient. FIG. 6 is a perspective view of an embodiment of the mixed bone replacement material 114 being dispensed from the syringe via a cannula or needle 112. In this embodiment, after filling the syringe barrel 108 with the desired amount of the bone replacement material 114, the second end of the plunger 106 is pushed in a retracted position causing first end of the plunger 110 to mover spacer 109 forward thereby expelling bone replacement material out of the tip 111 of the syringe and into cannula or needle 112 and to the desired site. In the embodiment shown, the spacer is complementary to at least the tip of the syringe and/or upper part of the syringe. The spacer fits within the syringe barrel and is substantially complementary in shape to the tip of the syringe and/or section just below the tip as shown by 109 in FIG. 6. The spacer can still move longitudinally in the syringe barrel with the sliding plunger, but is snug within the barrel and can not tilt to the side or move horizontally in the syringe, when the syringe is coupled to the container.

The cannula or needle 112 can be attached to the syringe tip 111 by a leur fitting or snap fit that can be the same or different from that which is used to attach the syringe to the bottom opening of the container. In some embodiments, the cannula or needle may optionally include one or more tapered regions. In some embodiments, the cannula or needle may be beveled. The cannula or needle may also have a tip style vital for accurate application based on the anatomic site for delivering the bone replacement material. Examples of tip styles include, for example, blunt tips, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the cannula or needle, among other things, will depend on the site for implantation. For example, the width of the bone fracture gaps are only about 1-5 mm. Thus, the needle or cannula, in various embodiments, can be designed for these specific areas. Some examples of lengths of the cannula or needle of the device may include, but are not limited to, from about 10 to 150 mm in length, for example, about 10 mm for wrist fracture use, about 40 mm for tibia/ankle fractures and about 110 mm for a femur fracture patient. The thickness of the cannula or needle will also depend on the site of application. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In some embodiments, the needle or cannula has a diameter of 5 to 7 mm.

In some embodiments, there is a method for mixing and dispensing bone cement, the method comprising: providing a container to mix and dispense bone cement, the container having a top opening for addition of bone cement, a bottom surface, and at least one bottom opening disposed in the bottom surface of the container for dispensing bone cement out of the bottom surface of the container when it is mixed; providing a syringe configured to receive bone cement dispensed from the container, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position, the syringe containing at least one spacer disposed within the syringe between the tip and the first end of the plunger, the spacer movable with the plunger and configured to contact the at least one bottom opening of the container and seal it when the plunger is moved in the retracted position so as to prevent dispensing of bone cement into the syringe, and the spacer configured to allow dispensing of bone cement into the syringe when the first end of the plunger is moved to the extended position to open the at least one bottom opening of the container; coupling the syringe tip to the at least one bottom opening of the container; adding bone cement to the top opening of the container and mixing it in the container; and moving the plunger to the extended position to move the spacer away from the at least one bottom opening of the container to dispense the bone cement into the syringe.

Bone Replacement Material

Bone replacement materials can include bone particles from fully mineralized bone, and demineralized bone particles and combinations thereof. The bone particles can be autograft, allograft, xenogenic, transgenic bone particles or a combination thereof.

In some embodiments, the bone replacement material includes bone cements. Bone cements are commonly provided in two or more components. The first component is usually a powder and the second component is usually in liquid form. Examples of bone cement materials include those based on acrylate materials which can react by polymerization to form acrylate polymers.

In some embodiments, the bone cement comprises powder that includes, for example, calcium phosphate based powders and poly-methyl-methacrylate based powders. Any of various osteoconductive powders, such as ceramics, calcium sulfate or calcium phosphate compounds, hydroxyapatite, magnesium and Si based cements, deproteinized bone, corals, and certain polymers, can alternatively or additionally be used in the bone cement.

Typically, a bone cement can be formed by mixing a liquid acrylate monomer with a powder such as acrylate polymer using a mixing element, where the mixing can be accomplished by hand or machine. The resulting mixture has a paste or dough-like consistency. Typically, the components of the mixture react, involving polymerization of the acrylate monomer and copolymerization with the acrylate polymer particles. The viscosity of the cement composition increases during the reaction, resulting in a hard cement. The curing reaction of a bone cement material is generally exothermic.

Typically, the bone cement is prepared prior to injection by mixing bone-cement powder (e.g., poly-methyl-methacrylate (PMMA)), a liquid monomer (e.g., methyl-methacrylate monomer (MMA)), an x-ray contrast agent (e.g., barium sulfate), and an activator of the polymerization reaction (e.g., N,N-dimethyl-p-toluidine) to form a fluid mixture. Other additives including but not limited to stabilizers, drugs, fillers, dyes and fibers may also be included in the bone cement. Since the components react upon mixing, immediately leading to the polymerization, the components of bone cement should be kept separate from each other until the user is ready to form the desired bone cement. Once mixed, the user must work very quickly because the bone cement sets and hardens rapidly.

Other examples of bone cement compositions and/or their uses are discussed in US Patent Publication No. 20080109003, U.S. Pat. No. 7,138,442; U.S. Pat. No. 7,160,932; U.S. Pat. No. 7,014,633; U.S. Pat. No. 6,752,863; U.S. Pat. No. 6,020,396; U.S. Pat. No. 5,902,839; U.S. Pat. No. 4,910,259; U.S. Pat. No. 5,276,070; U.S. Pat. No. 5,795,922; U.S. Pat. No. 5,650,108; U.S. Pat. No. 6,984,063; U.S. Pat. No. 4,588,583; U.S. Pat. No. 4,902,728; U.S. Pat. No. 5,797,873; U.S. Pat. No. 6,160,033; and EP 0 701 824, the disclosures of which are herein incorporated by reference.

In some embodiments, other additives can be mixed with the bone cement and this includes bioactive substances. Thus, one or more bioactive substances can be combined with the bone cement by soaking or immersing the bone cement in a solution or dispersion of the desired bioactive substance(s). Bioactive substances include physiologically or pharmacologically active substances that act locally or systemically in the host. In certain applications, the bone cement can be used as a time-release drug delivery device for drugs or other bioactive substances that are to be delivered to the surgical site.

Bioactive substances which can be readily combined with the bone cement include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin or gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents or polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; or nucleic acids. When employed, the total amount of bioactive substance can represent from about 0.1 to about 60 weight percent of the osteoimplant.

In some embodiments, the bioactive agent is mixed before, with or after the bone cement is added to the container. In some embodiments, the bioactive agent comprises the family of proteins known as the transforming growth factor-beta (TGFβ) superfamily of proteins, which includes the activins, inhibins, or bone morphogenetic proteins (BMPs). In some embodiments, the active agent includes at least one protein from the subclass of proteins known generally as BMPs. BMPs have been shown to possess a wide range of growth and differentiation activities, including induction of the growth and differentiation of bone, connective, kidney, heart, and neuronal tissues. See, for example, descriptions of BMPs in the following publications: BMP-2, BMP-3, BMP-4, BMP-5, BMP-6, and BMP-7 (disclosed, for example, in U.S. Pat. Nos. 5,013,649 (BMP-2 and BMP-4); 5,116,738 (BMP-3); 5,106,748 (BMP-5); 5,187,076 (BMP-6); and 5,141,905 (BMP-7)); BMP-8 (disclosed in PCT WO 91/18098); BMP-9 (disclosed in PCT WO 93/00432); BMP-10 (disclosed in PCT WO 94/26893); BMP-11 (disclosed in PCT WO 94/26892); BMP-12 or BMP-13 (disclosed in PCT WO 95/16035); BMP-15 (disclosed in U.S. Pat. No. 5,635,372); BMP-16 (disclosed in U.S. Pat. No. 6,331,612); MP52/GDF-5 (disclosed in PCT WO 93/16099); or BMP-17 or BMP-18 (disclosed in U.S. Pat. No. 6,027,917). The entire disclosure of these references is herein incorporated by reference. Other TGF-proteins that may be useful as the active agent of the bone cement paste include Vgr-2 and any of the growth and differentiation factors (GDFs), such as, for example, GDF-5.

A subset of BMPs that may be used in certain embodiments includes BMP-2, BMP-4, BMP-5, BMP-6, BMP-7, BMP-8, BMP-9, BMP-10, BMP-11, BMP-12 or BMP-13. In some embodiments, the composition contains two or more active agents (e.g., BMP-2 and BMP-4). Other BMPs and TGF-proteins may also be used.

The active agent may be recombinantly produced, or purified from another source. The active agent, if a TGFβ protein such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β (e.g., a heterodimer composed of one monomer each of a BMP and a related member of the TGF-β superfamily). Examples of such heterodimeric proteins are described, for example in published PCT Patent Application WO 93/09229.

In some embodiments, the amount of growth factor, (e.g., bone morphogenic protein) may be sufficient to cause bone growth. In some embodiments, the growth factor is rhBMP-2 and is contained in the bone replacement material in an amount of from 1 to 2 mg per cubic centimeter of the bone replacement material. In some embodiments, the amount of rhBMP-2 morphogenic protein is from 2.0 to 2.5 mg per cubic centimeter (cc) of the bone replacement material.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

The bone replacement material may be mixed with additional therapeutic agents. Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, or analgesic agent. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+) R and (−)-S enantiomers of the statin. In various embodiments, the statin may comprise a 1:1 racemic mixture of the statin.

One method of making the bone replacement material includes adding the powder to the container and adding the liquid and other components to the container and mixing them with a mixing element. The mixing element can be placed in or attached to the upper opening of the container and the mixing element stirred by hand or machine until the desired consistency of the slurry or paste or liquid is reached. Optionally, the mixture can include one or more other optional components such as any of binders, fillers, plasticizers, biostatic/biocidal agents, surface active agents, bioactive substances, or reinforcing components. The syringe is then filled with the bone replacement material and then delivered to the anatomic site as discussed above.

The bone replacement material can be injected at the desired anatomic site, for example, a hard tissue repair site, e.g., one resulting from injury, defect brought about during the course of surgery, infection, malignancy or developmental malformation, or the like. The bone replacement material can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal or metatarsal bones.

In some embodiments, the bone cement comprises two separate components, one component being liquid and a second component being solid and the bone cement is mixed with the top opening while being exposed to room air.

Kits

The mixing and delivery device and its components can be arranged as a kit shown in FIG. 1. One or more of the devices' components may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment. In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the mixing and delivery device may be packaged in a moisture resistant package and then terminally sterilized by gamma irradiation. In use the practitioner removes the one or all components from the sterile package for use. In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the mixing and delivery device and/or one or more components of its components (e.g., bone replacement material), including, but not limited to, gas sterilization, such as, for example, with ethylene oxide or steam sterilization.

In various embodiments, a kit is provided comprising sterile or non-sterile bone replacement material and/or diluents. The kit may include additional parts along with the mixing and delivery device combined together to be used with it (e.g., wipes, needles, syringes, etc.). The kit may include gloves, drapes, wound dressings and other procedural supplies for maintaining sterility of the delivery process, as well as an instruction booklet, DVDs, or CDs, which may include a chart that shows how to mix and use the device.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A bone replacement material mixing and delivery device, comprising:
   a container for mixing and holding bone replacement material, the container having a top opening for addition of bone replacement material, a bottom surface, and at least one bottom opening disposed in the bottom surface of the container for transfer of bone replacement material out of the bottom surface of the container;
   a syringe configured to receive bone replacement material from the container for delivery to a patient, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position; and
   at least one spacer disposed within the syringe between the tip of the syringe and the first end of the plunger, the spacer movable with the plunger and configured to contact the at least one bottom opening of the container and seal it when the plunger is moved in the retracted position so as to prevent transfer of bone replacement material into the syringe, and the spacer configured to allow transfer of bone replacement material into the syringe when the first end of the plunger is moved to the extended position to open the at least one bottom opening of the container.

2. A bone replacement material mixing and delivery device according to claim 1, wherein the spacer is a shape complementary to the tip of the syringe to plug the at least one bottom opening or the spacer mates with the at least one bottom opening.

3. A bone replacement material mixing and delivery device according to claim 1, wherein the spacer is a shape complementary to the tip of the syringe and a portion of a syringe barrel under the tip.

4. A bone replacement material mixing and delivery device according to claim 1, wherein the spacer is a size that extends out of the syringe when the plunger is moved to the retracted position to seal the at least one bottom opening.

5. A bone replacement material mixing and delivery device according to claim 1, wherein the spacer is a size that remains in the syringe when the plunger is moved to the retracted position to seal the at least one bottom opening.

6. A bone replacement material mixing and delivery device according to claim 1, wherein the container is a bowl and powder and liquid are mixed in the bowl to form the bone replacement material.

7. A bone replacement material mixing and delivery device according to claim 1, wherein the spacer is a size that extends out of the syringe when the plunger is moved to the retracted position to seal the at least one bottom opening and is flush with the bottom surface of the container.

8. A bone replacement material mixing and delivery device according to claim 1, wherein the spacer is a size that extends out of the syringe when the plunger is moved to the retracted position to completely expel the bone replacement material for delivery to the patient.

9. A bone replacement material mixing and delivery device according to claim 1, wherein the at least one bottom opening comprises a Luer Lock Fitting configured to allow the syringe tip to be removably coupled to the container.

10. A bone replacement material mixing and delivery device according to claim 1, further comprising a cover configured to close the top opening while mixing the bone replacement material, a stand to hold the container and syringe in an up right position, a spatula for mixing the bone replacement material, and a cannula for attaching to the syringe tip after it is filled with bone replacement material.

11. A bone replacement material mixing and delivery device according to claim 1, wherein the syringe is removably coupled to the at least one bottom opening of the container to provide fluid communication of the container to the syringe.

12. A bone cement mixing device, comprising:
    a container for mixing and holding bone cement, the container having a top opening for addition and mixing of bone cement, a bottom surface, and at least one bottom opening disposed in the bottom surface of the container for transfer of bone cement out of the bottom surface of the container;
    a syringe configured to receive bone cement from the container, the syringe having a tip configured to be removably coupled to the at least one bottom opening of the container, the syringe comprising a plunger slidable within the syringe, the plunger having a first end and a second end, the second end configured for moving the first end of the plunger to at least a retracted position within the tip of the syringe and an extended position; and
    at least one spacer disposed within the syringe between the tip of the syringe and the first end of the plunger, the spacer contacting the first end of the plunger and movable with the plunger, the spacer being a shape complimentary to the tip of the syringe and a portion of the syringe under the tip and configured to contact the at least one bottom opening of the container and seal it when the plunger is moved in the retracted position so as to prevent transfer of bone cement into the syringe, and the spacer configured to allow transfer of bone cement into the syringe when the first end of the plunger moving to the extended position to move the spacer away from the at least one bottom opening of the container.

13. A bone cement mixing device according to claim 12, wherein the spacer is a size that extends out of the syringe when the plunger is moved to the retracted position to seal the at least one bottom opening.

14. A bone cement mixing device according to claim 12, wherein the spacer is a size that remains in the syringe when the plunger is moved to the retracted position to seal the at least one bottom opening.

15. A bone cement mixing device according to claim 12, wherein the container is a bowl and powder and liquid are mixed in the bowl to form the bone cement.

16. A bone cement mixing device according to claim 12, wherein the spacer is a size that extends out of the syringe when the plunger is moved to the retracted position to seal the at least one bottom opening and is flush with the bottom surface of the container.

17. A bone cement mixing device according to claim 12, wherein the spacer is a size that extends out of the syringe when the plunger is moved to the retracted position to completely expel the bone cement for delivery to a patient.

18. A method for mixing and dispensing bone cement, the method comprising:
provided a container to mix and dispense bone cement, the container having a top opening for addition of bone cement, a bottom surface, and at least one bottom opening disposed in the bottom surface of the container for dispensing bone cement out of the bottom surface of the container when it is mixed;
providing a syringe configured to receive bone cement dispensed from the container, the syringe having a tip configured to be removably coupled to the at least one bottom opening of the container, the syringe comprising a plunger slidable within the syringe, the plunger having a first end and a second end, the second end configured for moving the first end of the plunger to at least a retracted position and an extended position, the syringe containing at least one spacer disposed within the syringe between the tip and the first end of the plunger, the spacer movable with the plunger and configured to contact the at least one bottom opening of the container and seal it when the plunger is moved in the retracted position so as to prevent dispensing of bone cement into the syringe, and the spacer configured to allow dispensing of bone cement into the syringe when the first end of the plunger is moved to the extended position to open the at least one bottom opening of the container;
coupling the syringe tip to the at least one bottom opening of the container;
adding bone cement to the top opening of the container and mixing it in the container; and
moving the plunger to the extended position to move the spacer away from the at least one bottom opening of the container to dispense the bone cement into the syringe.

19. A method for mixing and dispensing bone cement according to claim 18, wherein the bone cement comprises two separate components, one component being liquid and a second component being solid and the bone cement is mixed with the top opening while being exposed to room air.

20. A method for mixing and dispensing bone cement according to claim 18, wherein the container is a bowl and the bone cement is mixed with a spatula by inserting the spatula in the top opening.

* * * * *